(12) United States Patent
Perrier et al.

(10) Patent No.: US 8,741,359 B2
(45) Date of Patent: Jun. 3, 2014

(54) METHOD FOR TESTING A SUBSTANCE WHICH IS POTENTIALLY ACTIVE IN THE FIELD OF LIPOLYSIS AND ITS MAINLY COSMETIC USE

(75) Inventors: Eric Perrier, Les Côtes D'Arey (FR); Delphine Rival, Ternay (FR); Valérie Lamy, Lyons (FR)

(73) Assignee: BASF Beauty Care Solutions France S.A.S., Lyons (FR)

( * ) Notice: Subject to any disclaimer, the term of this patent is extended or adjusted under 35 U.S.C. 154(b) by 0 days.

(21) Appl. No.: 13/536,342

(22) Filed: Jun. 28, 2012

(65) Prior Publication Data

US 2012/0269910 A1  Oct. 25, 2012

Related U.S. Application Data (63) Continuation of application No. 09/888,824, filed on Jun. 25, 2001, now abandoned.

(30) Foreign Application Priority Data

May 3, 2001 (FR) ..................................... 01 05908

(51) Int. Cl.
    *A01N 65/00* (2009.01)
(52) U.S. Cl.
    USPC ......................................................... 424/725
(58) Field of Classification Search
    None
    See application file for complete search history.

(56) References Cited

U.S. PATENT DOCUMENTS

| | | | |
|---|---|---|---|
| 3,431,175 A | 3/1969 | Arima et al. |
| 3,875,007 A | 4/1975 | Kobayashi |
| 4,218,443 A | 8/1980 | Comai et al. |
| 4,229,538 A | 10/1980 | Yamada et al. |
| 4,301,244 A | 11/1981 | Kikuchi et al. |
| 4,304,864 A | 12/1981 | Numa et al. |
| 4,603,106 A | 7/1986 | Cerami et al. |
| 4,844,901 A | 7/1989 | Keplinger et al. |
| 5,162,359 A | 11/1992 | Harsanyi et al. |
| 5,244,798 A | 9/1993 | Takeda et al. |
| 5,855,917 A | 1/1999 | Cook et al. |
| 5,880,095 A | 3/1999 | Park et al. |
| 5,911,992 A | 6/1999 | Braswell et al. |
| 5,955,072 A | 9/1999 | Takahashi et al. |
| 6,039,949 A | 3/2000 | Pero |
| 6,307,038 B1 | 10/2001 | Takahashi et al. |
| 6,326,396 B1 | 12/2001 | Wagle et al. |
| 6,432,400 B1 | 8/2002 | Chapus |
| 6,500,610 B1 | 12/2002 | Pamukcu et al. |
| 6,783,949 B1 | 8/2004 | Muller et al. |
| 2001/0041708 A1 | 11/2001 | Halvorsen et al. |
| 2002/0052034 A1 | 5/2002 | Guegler et al. |
| 2004/0053281 A1 | 3/2004 | Hartand et al. |

FOREIGN PATENT DOCUMENTS

| | | |
|---|---|---|
| EP | 0371844 B1 | 7/1992 |
| EP | 0655235 B1 | 8/1996 |
| EP | 0919223 A4 | 1/2000 |
| EP | 1038518 A1 | 9/2000 |
| EP | 0993822 B1 | 6/2003 |
| FR | 1484662 A | 6/1967 |
| FR | 2350604 B1 | 8/1983 |
| FR | 2663848 A1 | 1/1992 |
| FR | 2748659 B1 | 7/1998 |
| FR | 2804605 B1 | 5/2002 |
| JP | 08012564 * | 1/1996 |
| JP | 08012564 B | 2/1996 |
| JP | 08127524 C | 5/1996 |
| JP | 09030949 A | 2/1997 |
| JP | 09059169 A | 3/1997 |
| JP | 09291042 A | 11/1997 |
| JP | 10182414 A | 7/1998 |
| JP | 10265363 A | 10/1998 |
| JP | 11269029 A | 10/1999 |
| JP | 2000028601 A | 1/2000 |
| JP | 2000103741 A | 4/2000 |
| JP | 2000336024 A | 12/2000 |
| WO | WO-82/01130 A1 | 4/1982 |
| WO | WO-8300930 A1 | 3/1983 |
| WO | WO-96/28008 A3 | 3/1997 |
| WO | WO-98/24422 A3 | 10/1998 |
| WO | WO-00/02571 A1 | 1/2000 |

OTHER PUBLICATIONS

"International Cosmetic Ingredient Dictionary and handbook Ninth Edition 2002" Editiors: Pepe et al. Published By: The Cosmetic, Toiletry, and Fragrance Association. Copyright 2001 CTFA.

Bensadoun et al., "Purification and Characterization of Lipoprotein Lipase from Pig Adipose Tissue", J. Biol. Chem., vol., 249, No. 7, (1974), pp. 2220-2227.

Carroll et al., "Inhibition of Mycocardial Lipoprotein Lipase by U-57,908 (RHC 60267)" Lipids, vol. 27, (1992), pp. 305-307.

Cheng et al., "C-Terminal Domain of Apolipoprotein C11 as Both Activator and Competitive Inhibitor of Lipoprotein Lipase", Biochemical Journal, vol. 269, No. 2, (1990), pp. 403-407.

(Continued)

*Primary Examiner* — Michael Meller
(74) *Attorney, Agent, or Firm* — Drinker Biddle & Reath LLP (57) ABSTRACT

A method of testing a substance potentially active in the field of lipolysis comprising: preparing a substrate containing at least one triacylglycerol; placing this substrate in contact with a substance potentially active in the field of lipolysis, and with a lipoprotein lipase, in the presence of a cofactor of lipoprotein lipase, for a period of time sufficient to release at least in part one fatty acid of the triacylglycerol; and determining the capacity of inhibition of the release of the fatty acid resulting from the activity of the lipoprotein lipase, under the action of said potentially active substance, and evaluating the result of the inhibition which is either compared to the result obtained in the absence of the potentially active substance tested or compared with the result obtained in the presence of a known inhibitor acting as reference. Cosmetic and pharmaceutical uses are described.

9 Claims, 2 Drawing Sheets

(56) References Cited

OTHER PUBLICATIONS

De Man et al., "Lipolysis of Very Low Density Lipoproteins by Heparan Sulfate Proteoglycan-Bound Lipoprotein Lipase", Journal of Lipid Research, vol. 38, (1997), pp. 2465-2472.
De Man et al., Atherosclerosis, vol. 136, (1998), pp. 255-262.
Encyclopedia American website, http://ea-ada.grolier.com, download from the Web on Dec. 2, 2004.
Feve, B., "L'Adipoycte, une cellute tres active que l'on commence á savior controller", Cosmetologie, No. 21, (1999), pp. 30-33 (English translation attached).
Goldberg, I., "Lipoprotein and Lipolysis: Central Roles in Lipoprotein Metabolism and Atherogenesis", Journal of Lipid Research, vol. 37, (1996), pp. 693-707.
Internet document, www.heifpflanze.ch/uncaria.htm (Jun. 27, 2003).
Itaru et al., "Effects of Shingomyelin and Cholesterol on Lipoprotein Lipase-Medicated Lipolysis in Lipid Emulsions", Journal of Lipid Research, vol. 39, No. 1, (1998), pp. 1431-1451.
Jain et al., "Anti-Inflammatory Principles from Natural Sources", Hamdard Medicus, vol. 36, No. 3, (1993), pp. 16-27.
Jong et al., Biochem. J., vol. 328, (1997), pp. 745-750.
Kubo et al., Biochim. Biophys. Acta, vol. 918, (1987), pp. 168-174.
Laus et al., "Alkaloids of Peruvian Uncaria Tomentosa", Phytochmeistry, vol. 45, No. 4, (1997), pp. 855-860.
NEFA-C Free Fatty Acid Determination Kit Instructions, accessed on the Internet at http://www.instruchmie.nl/instruhome.htm (and NEFA-C under N-products therein) on Aug. 27, 2003.
Nilsson-Ehle et al., "A Stable, Radioactive Substrate Emulsion for Assay of Lipoprotein Lipase", Journal of Lipid Research, vol. 17, (1976), pp. 536-541.
Nozaki et al., Clin. Chem., vol. 30, No. 5, (1984), pp. 748-751.
Patent Abstracts of Japan, vol. 2000, No. 15, & JP 2000 336024, "Cosmetic composition containing moisturizing plant extract", Dec. 5, 2000.
Posner et al., "The comparative Kinetics of Soluble and Neparin Sepharose Immobilized Bovine Lipoprotein Lipase EC-31.1.34", Archives of Biochemistry and Biophysics, vol. 226, No. 1, (1983), pp. 306-316.
Pradines-Figueres et al., "Lipoprotein Lipase Stored in Adipocytes and Muscle Cells is a Cryptic Enzyme", J. Lipid Res., vol. 31, (1990), pp. 1467-1476.
Quinn et al., "Lipoprotein Lipase: Mechanism of Action and Role in Lipoprotein Metabolism", Prog. Liquid Research, vol. 22, (1982), pp. 35-78.
Taber's Medical Dictionary, Thomas ed., 15th edition, (1985), F. A. Davis Company: Philadelphia, PA, p. 1313.
Vainio et al., "Inhibition of Lipoprotein Lipase by Benzene Boronic Acid Effect of Apolipoprotein C-11", Biochimica et Biophysica Acta., vol. 711, (1982), pp. 386-390.
Wang et al., "Effects of Albumin and Apolipoprotein C-11 on the Acyl-Chain Specifically of Lipoprotein Lipase Catalysis", J. Lipid Res., vol. 34, (1993), pp. 2091-2098.
Webster's Dictionary, (1984), Houghton-Mifflin: Boston, MA, pp. 689 and 1094.
Zambon et al., "Analysis of Techniques to Obtain Plasma for Measurement of Levels of Free Fatty Acids", Journal of Lipid Research, vol. 34, No. 6, (1993), pp. 1021-1028.

\* cited by examiner

METHOD FOR TESTING A SUBSTANCE WHICH IS POTENTIALLY ACTIVE IN THE FIELD OF LIPOLYSIS AND ITS MAINLY COSMETIC USE

The invention relates to a method of testing a substance which is potentially active in the field of lipolysis and its mainly cosmetic use.

The present invention essentially relates to a method of testing a substance which is potentially active in the field of lipolysis, the substances which are active in the field of lipolysis thus detected, and their use in the cosmetic or pharmaceutical field, especially for providing slimming care, for increasing the blood microcirculation, for improving the appearance of the skin and especially for diminishing <<orange peel>> appearance.

PRIOR ART RELATING TO SLIMMING PRODUCTS AND LIPOLYSIS

The lipolytic products developed in laboratories to this day possess slimming activities which are really efficient.

These products are in fact the result of strategies which take the whole of the mechanisms regulating lipolysis more and more into account. In summary, the development of slimming products implies recourse to:

1) Veinotonic active products;
2) Lipolytic active products which target the whole of the mechanisms implicated in the regulation of lipolysis.

Veinotonic active products have an action on the skin blood microcirculation. They have been used for a long time in the treatment of heavy legs and of oedemas or even for increasing capillary resistance and for participating in anti-inflammatory reactions. The veinotonic products thus constitute the active products of choice 1) for increasing the blood microcirculation and 2) for improving the appearance of the skin (diminishing <<orange peel>> appearance).

Lipolytic Active Products:

1) The key enzyme of lipolysis is hormono-sensitive lipase (HSL) which is an intracellular enzyme of the adipocytes. This lipase enables the destocking of adipocyte triglycerides by hydrolysis (by the HSLs) and degradation of the amino acids formed (by the cell). The lipolytic cosmetic active products thus seek to activate this enzyme with the aid of cofactors, or to prevent its inhibition.
2) HSL exists in two forms: the active form corresponds to the phosphorylation of the inactive form, the phosphorylation is effected by an enzyme, protein kinase (PKA) which is c-AMP-dependent, i.e. which needs cAMP in order to be active itself. The lipolytic cosmetic active products thus seek to activate this enzyme by attempting to have more cAMP produced in the cell, or in seeking to prevent the degradation of this cAMP.
3) cAMP is formed in the cell by virtue of a membrane enzyme, adenyl cyclase, which can be activated by stimulatory G-proteins (Gs) which are sensitive to beta-3 adrenergic receptors, or which can be inhibited by inhibitory G-proteins (Gi) which are sensitive to alpha-2 adrenergic receptors. A certain number of cosmetic active products have been developed so as to be able to interact with one or another of these receptors, so as to stimulate the adenyl cyclase and so as to increase the level of intracellular cAMP.
4) cAMP can also be hydrolyzed in the cell by virtue of an intracellular enzyme, phosphodiesterase (PDE) and other cosmetic active products have been developed so as to be able to inhibit this enzyme and so as to conserve a raised intracellular cAMP level.

AIMS OF THE INVENTION

The aim of the present invention is to provide a novel method of testing a substance which is potentially active in the field of lipolysis, which is safe and reliable and which enables the degree of lipolytic activity of a substance, and thus its capacity to act upon lipolysis, to be determined, to thus enable fatty deposits to be diminished, to be slowed down or to be reabsorbed, to enable having a slimming activity, to enable increasing the blood microcirculation, to enable improving the appearance of the skin and in particular to enable diminishing the particularly ugly <<orange peel>> appearance.

Another main aim of the present invention is to solve the novel technical problem consisting of providing a test method which is capable of finding substances which are active in the field of lipolysis, by a test method which has the lowest number of steps as possible, which is not expensive, which can be used on an industrial scale, especially in research laboratories, preferably automatically, and which thus enables the skill of the person carrying out the test to be freed as much as possible.

Yet another main aim of the present invention is to solve the novel technical problem consisting of providing a test method which enables finding novel substances which are active in the field of lipolysis, which has a great efficiency and which can be used for the preparation of novel cosmetic compositions, or even pharmaceutical compositions, which make use of such a lipolytic activity, especially within the context of an activity of diminishing, slowing down or reabsorption of fatty deposits, or of a slimming activity, or for improving the tone of the skin.

SUMMARY OF THE INVENTION

The present invention enables the whole of the aims set forth above to be met in a particularly unexpected manner, which was not obvious to the person skilled in the art.

Thus, the present invention provides a novel method of testing a substance which is potentially active in the field of lipolysis, which is based upon the capacity of inhibition of the enzyme lipoprotein lipase by a substance which is potentially active in the field of lipolysis that it tested.

The enzyme lipoprotein lipase or LPL is an enzyme which is produced by the adipocytes and which is secreted by exocytosis towards the endothelial cells of the blood capillaries, and which has the capacity to hydrolyse the ester bonds in position 1,3 of the triacylglycerols borne by the chylomicrons and the very low density lipoproteins (VLDL) circulating in the lumen of the blood vessels as described by I. J. Goldberg in the article "Lipoprotein lipase and lipolysis: central roles in lipoprotein metabolism and atherogenesis" published in the Journal of Lipid Research, 37, 693-707, (1996), for releasing fatty acids which are then captured by the adipocytes. It will be noted that the chylomicrons and the VLDLs are human plasma lipoproteins which transport the lipids towards the tissues, see D. Quin et al., in the article "Lipoprotein lipase: mechanism of action and role in lipoprotein metabolism" published in Prog. Lipid Res. 22, 35-78 (1982).

Furthermore, it will also be noted that the fatty acids transferred through the plasma membrane of the adipose cell will be lo taken up by the internal biochemical systems of the adipocyte in order to be stored again in the form of triacylglycerols, as demonstrated by B. Féve in the article "L'adipocyte, une cellule très active que l'on commence à savoir contrôler", published in Cosmetologie, N°21, 30-33 (1999).

Thus, the present invention is based on the novel concept which is firstly to provide a method of testing a substance which is potentially active in the field of lipolysis, preferably which is capable of acting upon the inhibition of the lipoprotein lipase, and secondly to make use of any substance having such an activity in the field of lipolysis, and in particular capable of inhibiting the activity of lipoprotein lipase, as a novel means of action for limiting the storage in the adipocyte.

Thus, under a first aspect, the present invention provides a method of testing a substance which is potentially active in the field of lipolysis, characterized in that it comprises the following steps:

a) preparing a substrate which contains at least one triacylglycerol;

b) placing this substrate in contact with a substance which is potentially active in the field of lipolysis, and with a lipoprotein lipase, in the presence of a cofactor of lipoprotein lipase, for a period of time which is sufficient for releasing at least in part one fatty acid of the triacylglycerol; and c) determining the capacity of inhibition of the release of the fatty acid resulting from the activity of the lipoprotein lipase, under the action of said potentially active substance, and evaluating the results of the inhibition which are compared to the result obtained in the absence of the potentially active substance tested or which are compared with the result obtained in the presence of a known inhibitor acting as reference.

Thus, the person skilled in the art easily understands that when the results of inhibition of the substance which is potentially active are significantly greater than the control, i.e. without active substance, or which are similar or significantly greater than a reference inhibitor, the activity of the substance in the lipolytic field can be characterized, i.e. confirmed or not.

Within the context of the invention, it is noted that the test method makes use of a determination of the fatty acids which are released from the acylated part or triacylated part of the triacylglycerol, or non-esterified fatty acids.

According to an advantageous variant, this method is characterized in that the lipoprotein lipase used originates from bovine milk or is of bacterial origin.

According to another variant, the method is characterized in that the triacylglycerol mentioned above comprises an acyl part which is obtained from a long chain fatty acid, preferably comprising 12 to 30 saturated or unsaturated carbon atoms in a straight or branched chain, more preferably mainly present in food. Preferably, the triacylglycerol comprises or is constituted of triolein.

According to an advantageous characteristic of the method according to the invention, the method is characterized in that the lipoprotein lipase is present with said cofactor which comprises or is constituted of apolipoprotein C-II, preferably of human origin.

According to another advantageous variant of the method according to the invention, the method is characterized in that the lipoprotein is placed in contact with the substrate in the presence of a fatty acid-acceptor substance or fatty acid-sequestering substance which prevents the blockage of the enzymatic activity of the lipoprotein lipase. Advantageously, the fatty acid-acceptor substance or fatty acid-sequestering substance comprises or is constituted by bovine or human albumin.

According to a particularly advantageous embodiment of the method according to the invention, the method is characterized in that the capacity of inhibition of the lipoprotein lipase by the potentially active substance is carried out in several steps:

a) first of all, the lipoprotein lipase is incubated for a determined period of time in the presence of the substance which is potentially active as inhibitor, b) the substrate which contains the triacylglycerol is incubated in the presence of the lipoprotein lipase cofactor, which preferably comprises or is constituted by apolipoprotein C-II, c) the mixture of the triacylglycerol/lipoprotein lipase cofactor which is preferably apolipoprotein C-II, is incubated in the presence of the enzyme lipoprotein lipase with or without the potentially active substance tested for its capacity of inhibition of the lipoprotein lipase, d) upon completion of this incubation, a determination is made upon the reaction medium of the non-esterified fatty acids by a technique which is available to the person skilled in the art, and e) a comparison is made of the capacity of inhibition of the release of a fatty acid of the triacylglycerol, or non-esterified fatty acid, resulting from the activity of the lipoprotein lipase in the presence of the potentially active substance tested, compared with the result obtained in the absence of the potentially active substance tested, or compared with the result obtained in the presence of a known inhibitor acting as reference.

According to a variant of this embodiment, the determination of the non-esterified fatty acids is made upon the reaction medium by an enzymatic technique, preferably in order to be followed by colorimetry at a wavelength determined by the enzymatic technique selected, and in this case the lowering of the optical density obtained at this wavelength is determined with respect to the control or to the reference inhibitor.

According to an even more advantageous variant, the determination of the non-esterified fatty acids is made upon the reaction medium by an enzymatic technique which can be followed by colorimetry at 550 nm and an inhibition is determined of the optical density at 550 nm which expresses a decrease in the fatty acids synthesized in the reaction medium, which is compared with the control or with a reference inhibitor, and the positive or negative activity is determined of said substance tested within the context of the observation of a significant or non-significant inhibition effected by said substance tested with respect to the control or to a reference inhibitor.

According to another particularly advantageous variant of the method according to the invention, the test is carried out of a substance which is potentially active in the field of lipolysis selected from the group consisting of an extract of fucus; an extract of dulse palmaria palmata; an extract of wheat proteins; an extract of spiruline; an extract of honeysuckle; an extract of St. John's wort; an extract of rice proteins; an extract of liana; an extract of potato; an extract of shiitake; an extract of fresh salmon; an extract of pumpkin; and an extract of lemon. These extracts are advantageously obtained by a solvent extraction procedure which preferably comprises an is aqueous or water extraction, or an alcoholic extraction, or a hydro alcoholic extraction, or a hydro glycolic extraction, in particular with ethylene glycol, propylene glycol or butylene glycol, or any mixtures of these solvents.

According to a particularly advantageous embodiment, the above-mentioned test is carried out with an extract of St. John's wort.

According to another advantageous variant of the invention, the test is carried out with an extract of liana, preferably an extract of Peruvian liana, known as liana *Uncaria tomentosa*.

According to yet another advantageous embodiment of the invention, the method is characterized in that a substance is identified for its lipolytic activity, in particular its slimming activity, from the test of inhibition mentioned above.

According to a second aspect, the present invention also covers the use of the test method mentioned above for evaluating the activity of a substance which can be used in a cosmetic composition or for preparing a medicament with a view to treating fatty deposits, especially by lipolysis, or for a slimming activity, as well as for evaluating the effectiveness of a slimming care or treatment applied to a subject.

According to a third aspect, the present invention also covers any substance which is active in the field of lipolysis characterized in that its activity in the field of lipolysis has been evaluated by a test method as defined above or as resulting from the following description.

According to a fourth aspect, the present invention also covers the use of a substance the activity of which in the field of lipolysis has been evaluated by the test method described above or described in the following description, as one of the lipolytic active agents in a cosmetic composition for decreasing, slowing down or reabsorbing fatty deposits, for a slimming activity, or for increasing the blood microcirculation, for improving the appearance or the tone of the skin, in particular for diminishing « orange peel» appearance.

According to a fifth aspect, the present invention even covers the use of a substance the activity of which in the field of lipolysis has been evaluated by the test method mentioned above or resulting from the following description, as one of the lipolytic active agents for preparing a medicament with a view to treating a pathology resulting from an excess of fatty deposits.

The invention further covers the use of an extract of liana *Uncaria tomentosa* as one of the principles having lipolytic or slimming activity in a cosmetic composition.

The invention further covers the use of an extract of St. John's wort as one of the active agents having lipolytic or slimming activity in a cosmetic composition.

According to a sixth aspect, the present invention further covers a cosmetic composition, characterized in that it comprises an effective amount of liana *Uncaria tomentosa* as one of the active agents having lipolytic or slimming activity in a cosmetically acceptable excipient.

The invention further covers a cosmetic composition, characterized in that it comprises an effective amount of an extract of St. John's wort as one of the agents having lipolytic or slimming activity.

According to a seventh aspect, the invention further covers a method of cosmetic care, characterized in that a cosmetic composition, comprising an active substance having lipolytic or slimming activity, the activity of which has been determined by the test method as defined above or as resulting from the following description taken as a whole, is applied topically on the skin.

According to a particular embodiment, the invention further covers a method of cosmetic care, characterized in that a cosmetic composition comprising an extract of liana *Uncaria tomentosa* as one of the active agents having lipolytic or slimming activity is applied topically on the skin.

According to another particular embodiment, the invention further covers a method of cosmetic care characterized in that a cosmetic composition comprising an extract of St. John's wort as one of the active agents having lipolytic or slimming activity is applied topically on the skin.

Within the context of any one of the above aspects or embodiments of the invention, the substance active in the field of lipolysis can be used in an amount which is sufficient for obtaining the lipolytic effect sought after for decreasing, slowing down or reabsorbing fatty deposits, for a slimming activity, for increasing the blood microcirculation, for improving the appearance or the tone of the skin, in particular for diminishing « orange peel» appearance. The concentration of use of said substance will vary as a function of the nature of the substance itself. In general, the concentration of the substance or of a plant extract comprising or constituting the active substance, in a broad sense, will be between 0.01% and 70% by weight, better between 0.01% by weight and 30% by weight, preferably between 0.5% and 20% by weight. The commercial concentrations will generally be from 0.01% to 30% by weight as shown in the formulation Examples 2 to 6.

The present invention shall be better understood by the person skilled in the art from the following description describing the preferred embodiment of the method of testing a substance which is potentially active in the field of lipolysis according to the present invention, which is given simply as an illustration and which in no way limits the scope of the invention. Equally, actually preferred examples of substances the activity of which has been demonstrated in the field of lipolysis within the context of the test method according to the invention are given simply as an illustration and in no way limit the scope of the test method according to the invention.

Furthermore, any characteristic which appears novel from the description taken as a whole, including the Examples and completed by the annexed Figures, is claimed as such, in its function as well as in its general mode of action. The examples of cosmetic or pharmaceutical composition will similarly also be given in an illustrative manner. In the Examples, all the percentages are given by weight, unless indicated otherwise, the temperature is in degrees C. unless indicated otherwise, and the pressure is atmospheric pressure, unless indicated otherwise.

DESCRIPTION OF THE DRAWINGS

FIG. 3 shows the comparison of inhibiting activity of the extract of liana *Uncaria tomentosa* subject matter of FIGS. 1 and 2 with the results obtained under the same testing conditions with an extract of St John's wort obtained by extraction with an aqueous glycolic solvent mixture, consisting of 40 weight percent of water/60 weight percent of butylene glycol, under the action of lipoprotein lipase, the concentration of active substance in formulation being shown in abscissa and the relative percentage of inhibition being shown in ordinate, the result with the extract of *Uncaria tomentosa* being shown on the right blocks with oblique lines uprising in the right direction whereas the results obtained with the St John's wort being shown on the left blocks with oblique lines going downwardly in the right direction.

EXAMPLE 1 OF THE INVENTION RELATING TO THE IMPLEMENTATION OF A METHOD OF TESTING A SUBSTANCE EVENTUALLY ACTIVE IN THE FIELD OF LIPOLYSIS

I—Study Model for Determining the Lipolytic Activity

The study of the inhibition of the lipoprotein lipase is carried out in an acellular in vitro model which is desired to be a most « intelligent» reflection possible of the situation encountered in vivo.

The LPL used in the study model retained does in fact originate from bovine milk, this choice having been determined by a very high homology (97%) of this enzyme with its human equivalent (A. Tatina et al, "La séquence en acides aminés de la lipoprotéine lipase humaine a été comparée à celle du lait bovin selon le programme BLAST 2 SEQUENCES», "Blast 2 sequences-a new tool for comparing protein and nucleotide sequences" published in FEMS Microbil Lett.,174, 247-250, (1999)); it is placed in the presence of a substrate, triolein, which is a triacylglycerol constituted of 3 oleic acid chains, (long chain fatty acids which are mainly found in food).

Triolein is the most representative substrate of the situation encountered in vivo since a study of the analysis of the fatty acids present in the adipocyte reveals (T. Raclot, et al, "Selective release of human adipocyte fatty acids according to molecular structure" published in Biochem. J., 324, 911-915, (1997); "Cholesteryl ester transfer activity in liver disease and cholestasis, and its relation with fatty acid composition of lipoprotein lipids" Clinica Chimica Acta, 248, 157-174, (1996)) that oleic acid is mainly present therein and thus constitutes the main product of hydrolysis of the lipoprotein lipase.

To the reaction medium are also added:

The cofactor of LPL, apolipoprotein C-II (apoCII) of human origin, which has a determining role in the hydrolysis of triacylglycerols by LPL (Posner et al, "Kinetics of product inhibition and mechanisms of lipoprotein lipase activation by apolipoprotein CII" published in Biochemistry, 26, 3771-3717, (1987)). ApoCII is fixed onto the triacylglycerols of the blood and enables a change in the confirmation of the LPL to be induced which is indispensable for the recognition of the substrate by the active site of the enzyme (Santamarina-Fojo S. and Dugi K. A. "Structure, function and role of lipoprotein lipase in lipoprotein metabolism published in Current Opinion in Lipidology, 5, 117-125, (1994)).

A fatty acid acceptor constituted by bovine albumin. LPL is an enzyme which has a significant affinity for its reaction product. The fatty acids released will in fact aggregate around the enzyme which will as it were be sequestered by the fatty acids and will therefore be no longer accessible to the substrate. The use of albumin which has a very high affinity for fatty acids enables the enzymatic activity of the LPL not to be blocked (Bengtsson-Olivecrona G. and Olivecrona T. "Phospholipase activity of milk lipoprotein lipase" published in Methods in enzymology, 197, 345-356, (1991)).

II—Inhibition of the Lipoprotein Lipase:

The study of the inhibition of LPL is effected according to the invention here preferably in two steps:

The enzyme is incubated for a determined period of time in the presence of its inhibitor while the triolein is incubated in the presence of apoCII so as to mimic the situation encountered in vivo.

The triolein/ApoCII mixture is then incubated in the presence of the medium constituted by the enzyme±inhibitor.

Upon completion of this incubation, a determination of the non-esterified fatty acids (NEFA) is effected upon the reaction medium by an enzymatic technique which is possible to be followed by colorimetry at 550 nm (NEFA-C kit).

A control corresponding to the LPL activity in the absence of inhibitor is effected. The use of an active product which is capable of modifying the enzymatic activity will be expressed as a lowering of the OD at 550 nm, i.e. a decrease in the fatty acids synthesized in the medium with respect to the control. The results are expressed in percentage inhibition with respect to the control.

1—Reference Lipoprotein Lipase Inhibitors:

It has been possible for reference inhibitors, cited in the literature (Korn E. D. "Clearing factor, a heparin-activated lipoprotein lipase" published in J.Biol. Chem. 215, 1-14, (1955); Quinn D. M. et al, "Lipoprotein lipase catalysed hydrolysis of water-soluble p-nitrophenyl esters. Inhibition by apolipoprotein C-II" published in Biochemistry, 21(26), 6872-6879, (1982); Greten H. et al, "Comparison of assay methods for selective measurement of plasma lipase" published in Atherosclerosis, 26, 563-572, (1977)), to be tested in our model and have given the following results:

TABLE 1

| Inhibitors (initial concentration) | Inhibition (%) | | |
|---|---|---|---|
| | Pure product | Pure product diluted to a 1/100th | Pure product diluted to a 1/10,000$^{th}$ |
| Protamine sulphate (0.4%) | 10.1% ± 7.9 | 2.6% ± 14.4 | 11.8% ± 14.7 |
| Protamine (2.4%) | 11.2% ± 6.6 | 9.6% ± 5 | 8.5% ± 8.7 |
| Sodium pyrophosphate (6%) | 15% ± 12.6 | 13% ± 12.5 | 0.4% ± 8.3 |

The inhibitors cited in the literature do not seem to be extremely potent inhibitors of LPL since the levels of inhibition observed at the concentrations tested are relatively modest; they are described in the scientific literature for being inhibitors which act by competition with the substrate of the enzyme.

2—Protein Denaturing Products:

It has been possible for denaturing products such as tannins and flavonoids, which are known for precipitating proteins, to be evaluated and the results are listed in Table 2.

TABLE 2

| Denaturing product | Inhibition | | |
|---|---|---|---|
| | Pure product | Pure product diluted to a 1/100th | Pure product diluted to a 1/10,000th |
| Tannic acid | 98.3% ± 12.4 | 11.4% ± 10.39 | 0% ± 9.8 |
| Grape OPC* | 99.3% ± 17.5 | 0% ± 1.5 | 0% ± 5.6 |

*OPC = Oligomers Procyanidolic, which are polyphenols

3—Screening of Active Products by the Method According to the Invention:

By the method according to the invention, a screening of about a hundred molecules has been carried out, in order to select, amongst various families of potential active principles, namely plant extracts, algae, polysaccharides or proteins, those having a strong LPL inhibiting activity. All the extracts were made according to protocols described in paragraphs III-1-b.

The levels of inhibition are evaluated at two different concentrations in order to compare the inhibitory activity of the various compounds.

Table 3 below gathers together some inhibition percentages obtained:

TABLE 3

|  | Inhibition of the pure extract (%) | Inhibition of the extract diluted to 1% (%) |
|---|---|---|
| Extract of *fucus* | 39 | 34 |
| Extract of dulse *palmaria palmata* | 49 | 19 |
| Extract of wheat proteins | 71 | 69 |
| Extract of *spiruline* | 66 | 47 |
| Extract of honeysuckle | 79 | 21 |
| Aqueous extract of lemon* | 53 | 12 |
| Extract of St. John's wort | 86 | 33 |
| Extract of rice proteins | 24 | 0 |
| Extract of liana | 98 | 50 |
| Extract of potato | 27 | 5 |
| Extract of shiitake | 47 | 41 |
| Extract of fresh salmon | 1.1 | 0.4 |
| Extract of pumpkin | 30 | 60 |
| Aqueous butylene glycol (60/40 w/w) extract of lemon** | 6.2 | 5.9 |

*5 weight percent of lemon powder available in the market for 95 weight percent of water
**5 weight percent of lemon powder available in the market for 95 weight percent of the aqueous butylene glycol mixture (60/40 w/w)

Upon completion of this study, a specific extract made from a very particular liana from South America (*Uncaria tomentosa*) was selected on the basis of its high activity.

III—The Active Products Selected

1—Extract of Liana or *Uncaria tomentosa* or Cat's Claw:
a) Generalities

Cat's Claw is a plant belonging to the Rubiaceae family, named *Uncaria tomentosa*. Cat's Claw is a liana which attaches itself to the trees of Amazonian forest with the aid of claws which are situated at the base of the leaves and which resemble those of a cat, hence its name. The plant is harvested above all in Peru and in the center of South America. The plant lives in moist media at an altitude ranging between 400 and 800 meters.

The tradition of the Indians of Peru attributes multiple virtues to this liana. They use bark extracts for gastric and intestinal problems and for diverse inflammation troubles. Moreover, the decoction is used against several types of infection, in topical use as well as in systemic use. The capacity of preventing illness and of curing tumors and cancers are attributed to it. A normalizing effect upon the feminine menstrual cycle and possibilities of contraceptives has also been reported (Karl-Heinz Reinhard "*Uncaria tomentosa* (Willd.) D.C.: Cat's claw, Una de gato, or Savéntaro" published in The Journal of Alternative and Complementary Medicine, vol.5, N°2, 143-151, (1999)).

*Uncaria tomentosa* exists in the United States under several forms of product for therapeutic application: asthma, cancer, illness prevention, fever, gastric ulcers, haemorrhages, inflammations, rheumatism, inflammation of the urinary passages, impurity of the skin . . . (Keplinger Klaus, et al, "*Uncaria tomentosa* (Willd.) DC-Ethnomedicinal use and new pharmacological, toxicological and botanical results" published in Journal of Ethnopharmacology, 64, 23-34, (1999)). Numerous pieces of research work are carried out on this liana over the last ten years.

In nature, *Uncaria tomentosa* exists as two chemical types, which contain either tetracyclic oxindole alkaloids (ryncho-phylline and isorhyncophylline), or pentacyclic oxindole alkaloids (pteropodine, isopteropodine, speciophylline, uncarine F, mitraphylline and isomitraphylline) in their roots. According to the chemical type, the properties of *Uncaria tomentosa* are not the same (Laus Gerhard, Brossner Dagmar and Keplinger Klaus "Alkaloids of Peruvian *Uncaria tomentosa*" published in Phytochemistry, vol. 45, N°4, 855-860, (1997)).

It has been shown that *Uncaria tomentosa* possesses an anti-inflammatory activity. This property would mainly be due to the quinovic acid glycosides which are present in the bark of this liana. An aqueous extract of the bark of Cat's Claw enables the cell toxicity, induced by peroxynitrite in degrading it, to be inhibited. It inhibits the expression of inducible nitric oxide synthase (iNOS) inhibiting the activation of NF-κB which diminishes the production of NO. It has been demonstrated that this anti-inflammatory activity would be due to the combination of all the glycosides present in the liana (Sandoval-Chacon M. et al, "Anti-inflammatory actions of Cat's claw: the role of NF-KB" published in Aliment Pharmacol Ther 12, 1279-1289, (1998)).

In addition to these anti-inflammatory properties, protective anti-mutagenic effects have been demonstrated in vivo against photomutagenesis by the Ames test ((Karl-Heinz Reinhard "*Uncaria tomentosa* (Willd.)D.C.: Cat's claw, Una de gato, or Savéntaro" published in The Journal of Alternative and Complementary Medicine, vol.5, N° 2, 143-151, (1999)).

*Uncaria tomentosa* of the pentacyclic oxindole alkaloids (POA) type increases the level of phagocytosis by the granulocytes. Moreover, it increases the proliferation of the human B and T lymphocytes via the endothelial cells. The POAs induce the endothelial cells in vitro in order to release a factor into the supernatant which regulates the proliferation of the lymphocytes. *Uncaria tomentosa* inhibits the proliferation of the lymphoblasts and the lymphoblastoid cell lines. These alkaloids act as a regulator of human immune responses (Wurm Martin, et al, "Pentacyclic Oxindole Alkaloids form *Uncaria tomentosa* induce human endothelial cells to release a lymphocyte-proliferation-regulating factor" published in Planta Medica, 64, 701-704, (1998)).

The glycosides of quinovic acid and steroids present in *Uncaria tomentosa* would possess an anti-viral activity against vesicular stomatitis virus at values of minimal inhibitory concentrations of 20-60 mg/ml. An anti-leukaemic activity has been demonstrated by the POAs which inhibit the growth of leukaemic HL60 and U937 cells (Keplinger Klaus, et al, "*Uncaria tomentosa* (Willd.) DC-Ethnomedicinal use and new pharmacological, toxicological and botanical results" published in Journal of Ethnopharmacology, 64, 23-34, (1999)).

*Uncaria tomentosa* would stimulate also the production of interleukins IL1 and IL6 by macrophages. It would thus possess an immuno-stimulant action (Lemaire I. et al, "Stimulation of interleukin-1 and -6 production in alveolar macrophages by the neotropical liana, *Uncaria tomentosa* (uña de gato) published in Journal of Ethnopharmacology 64, 109-115, (1999)).

b) Anti-lipoprotein Lipase Activity of *Uncaria tomentosa*:
b1-a) Preparation of an Aqueous-alcohol Extract of the Peruvian Liana *Uncaria tomentosa*

An alcoholic extract is prepared from the bark and/or the roots of the entire Peruvian liana plant *Uncaria tomentosa*, which is commercially available, in the following manner:

50 grams of bark or 30 grams of the entire plant, are ground very finely.

500 ml of an aqueous ethanolic solution at 70% v/v ethanol is added to the ground material. Heat is given at 65° C. and heating under reflux is effected for 2 hours. The alcohol is then evaporated off and the precipitate remaining in the aqueous solution is then removed by centrifugation. The supernatant obtained can be used as such or, preferably, can be lyophilized, and constitutes the dry liana extract used according to the invention according to paragraph b2 below and especially for preparing a cosmetic composition.

b1-b) Preparation of an Aqueous extract of the Peruvian Liana *Uncaria tomentosa*.

The extraction is made as described in paragraph b1-a except in the presence of water without the need for heating, for example at a temperature between 15 and 35° C., advantageously at ambient temperature.

The insoluble material is removed by centrifugation and the supernatant obtained in the form of an aqueous solution can be used preferably as such and especially for preparing a cosmetic composition.

b1-c) Preparation of an Aqueous Glycolic Extract of the Peruvian Liana *Uncaria tomentosa*.

The extraction is made as described in paragraph b1-a, except in the presence of a water/butylene glycol mixture, in the cold, in proportions which can range from 80/20 to 20/80. The same protocol is carried out with a water/propylene glycol mixture without the need for heating, for example at a temperature between 15 and 35° C., advantageously at ambient temperature, in proportions which can range from 80/20 to 20/80, or even with glycerol without the need for heating, for example at a temperature between 15 and 35° C., advantageously at ambient temperature in proportions which can range from 80/20 to 20/80.

The insoluble material is removed by centrifugation and the aqueous-glycolic supernatant obtained can be used preferably as such and especially for preparing a cosmetic composition.

b2) Determination of the Non-esterified Fatty Acids or NEFAs with the Commercial NEFA-C Determination Kit from Wako (from Oxoïd, 69571 Dardilly Cedex, France)

A study of the inhibitory activity of a 2% liana extract (2 g of lyophilisate prepared according to paragraph b1-a qsp 100 g water) containing 0.2% sodium methylparaben and 15% of butylene glycol at various concentrations of use was carried out fourfold. The results obtained are listed in Table 4 below and in FIG. 1:

TABLE 4

Concentrations of use of the 2% *Uncaria tomentosa* extract

Figure 1:
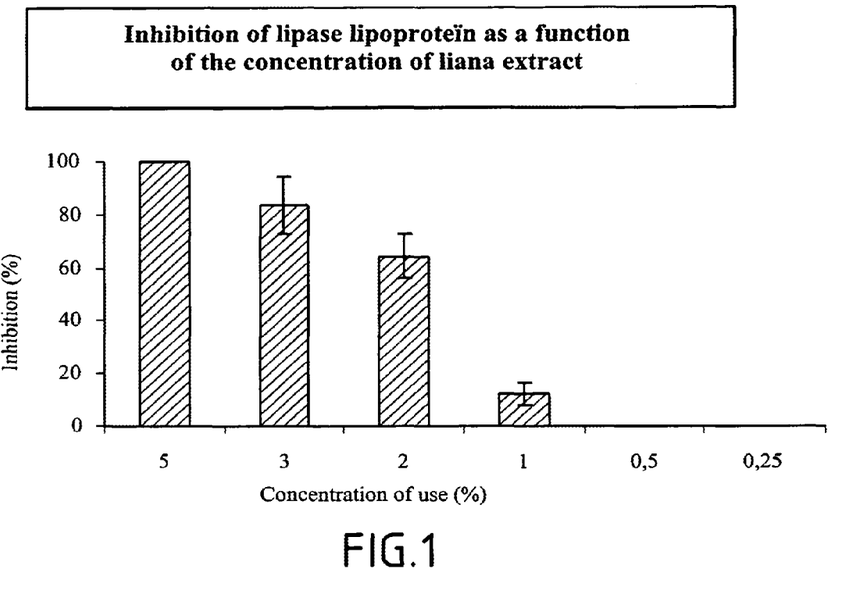
FIG. 1 shows inhibition of a lipoprotein lipase in function of the concentration in an aqueous-alcohol extract of liana *Uncaria tomentosa*, showing in abscissa the concentration of use in weight percent and in ordinate the inhibition of lipoprotein lipase obtained in relative percent; the said determination being performed of the non esterified fatty acids or NEFAs with commercial NEFA-C determination kit from Wako from oxold, 69571 Dardilly cedex France

|  | 5% | 3% | 2% | 1% | 0.5% | 0.25% |
|---|---|---|---|---|---|---|
| Inhibition (%) | 99.7 | 83.2 | 64.3 | 12.2 | 0 | 0 |
| Standard deviation (%) | 36.3 | 10.7 | 8.4 | 4.0 | 1.8 | 1.7 |

It results from Table 4 and FIG. 1 that the liana extract selected has a lipoprotein lipase inhibiting activity which is potent and which is in a « dose-dependent» manner, in contrast to the « potential» inhibitors cited in the literature.

The liana extract is consequently positioned as a very potent active product and very innovative in the field of slimming agents.

b3) Determination of the NEFAs by Gas Phase Chromatography or GPC:

In order to confirm the results of inhibition obtained with *Uncaria tomentosa* by use of the NEFA-C kit, the fatty acids released in the reaction medium by LPL are analyzed by GPC.

For this, an oleic acid determination technique which enables the oleic acid at the end of the enzymatic reaction to be quantified, was developed.

The oleic acid is extracted from the reaction medium of the enzymatic determination with ethanol, and then injected onto a commercial column from DBJW scientific: reference DB FFAP, 15 m in length, 0.32 mm internal diameter, 0.25 μm thickness in splitless mode. The temperatures of the injector and of the detector are 280° C. The programming in temperature starts at 50° C. for 1 minute and then rises by 40° C./minute up to 200° C. and then by 15° C. par minute up to 250° C. for 3 minutes. The retention time of oleic acid under these conditions is 7.74 minutes.

Certain reference inhibitors are re-tested by this technique by GPC, such as sodium pyrophosphate and protamine sulphate as well as tannic acid as denaturing product.

The results obtained are listed in Table 5 below.

TABLE 5

| | Inhibition | | |
|---|---|---|---|
| Inhibitors or denaturing product (initial concentration) | Pure product | Pure product diluted to a 1/100th | Pure product diluted to a 1/10,000th |
| Sodium pyrophosphate (6%) | 35.1% ± 11.1 | 30.4% ± 4.0 | 47.4% ± 10.4 |
| Protamine sulphate (0.4%) | 17.9% ± 17.5 | 5.0% ± 9.6 | 27.7% ± 2.9 |
| Tannic acid | 100% ± 1.8 | 44.8% ± 10.6 | 0% ± 3.8 |

The 2% extract of *Uncaria tomentosa* which is the subject of the test of determination of the NEFAs with the NEFA-C kit, namely 2 g qsp 100 g of water, and which contains 0.2% of sodium methylparaben and 15% of butylene glycol, is tested on LPL at various concentrations of use fourfold. The fatty acids released are therefore analyzed by GPC. The results obtained are listed in Table 6 and in FIG. 2:

TABLE 6

Concentration of use of 2% *Uncaria tomentosa* extract

Figure 2:
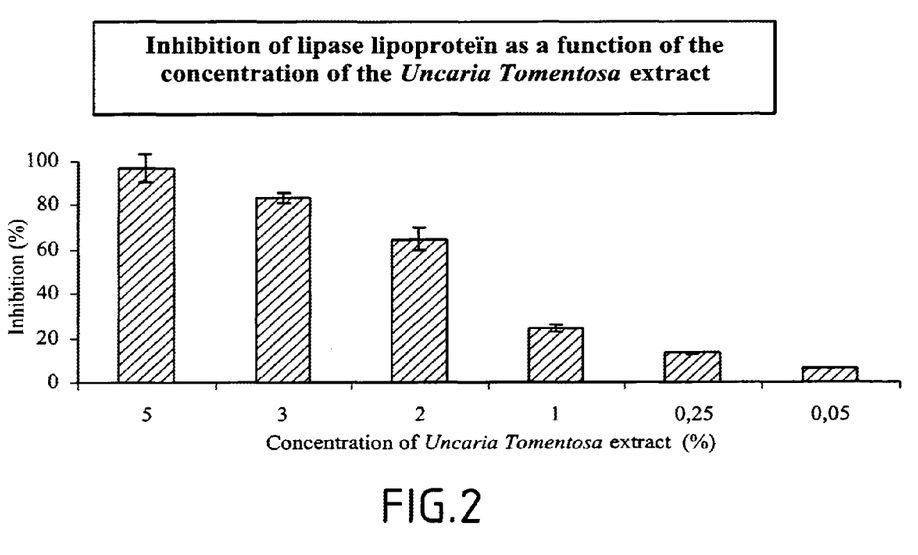
FIG. 2 represents the results obtained in the same conditions as FIG. 1 but the fatty acids released in the reaction medium are analyzed by gas phase chromatography or GPC.

| | 5% | 3% | 2% | 1% | 0.25% | 0.05% |
|---|---|---|---|---|---|---|
| Inhibition (%) | 96.8 | 83.6 | 64.8 | 24.4 | 13 | 6.2 |
| Standard deviation (%) | 6.2 | 2.5 | 5.2 | 1.5 | 0.1 | 0.1 |

The analysis by GPC confirms the results obtained with the determination kit.

The GPC has a high sensitivity in the low percentages of inhibition. In fact, the inhibitions obtained for the reference inhibitors and tannic acid are higher.

In contrast, the inhibitions obtained with the liana by GPC or by the kit for a concentration of use of between 2 and 5% are exactly the same. Below 2%, GPC will detect an inhibition while the kit will not.

These results confirm the fact that the liana *Uncaria tomentosa* is a very potent inhibiting active product of lipoprotein lipase.

2) Other Active Product Selected for the Inhibition of LPL: Extract of St. John's Wort 2.1) Preparation of the Extract of St. John's Wort An extract of St. John's wort is prepared from flower heads (flowers and/or buds) of the plant St. John's wort, which is commercially available, according to the following procedure:

2.1-a) Preparation of an Aqueous-alcohol Extract of St. John's Wort 50 grams of flower heads are ground very finely.

500 ml of an aqueous ethanolic solution at 70% v/v ethanol is added to the ground material. Heat is given at 65° C. and heating under reflux is effected for 2 hours. The alcohol is then evaporated off and the precipitate remaining in the aqueous solution is then removed by centrifugation. The supernatant obtained can be used as such or, preferably, can be lyophilized, and constitutes the dry St. John's wort extract used according to the invention according to 2.2 below and especially for preparing a cosmetic composition.

2.1-b) Preparation of an Aqueous Extract of St. John's Wort.

The extraction is made as described in paragraph 2.1-a except in the presence of water without the need for heating, for example at a temperature between 15 and 35° C., advantageously at ambient temperature.

The insoluble material is removed by centrifugation and the supernatant obtained in the form of an aqueous solution can be used preferably as such especially for preparing a cosmetic composition.

2.1-c) Preparation of an Aqueous Glycolic Extract of St. John's Wort.

The extraction is made as described in paragraph 2.1-a, except in the presence of a water/butylene glycol mixture without the need for heating, for example at a temperature between 15 and 35° C., advantageously at ambient temperature, in proportions which can range from 80/20 to 20/80. The same protocol is carried out with a water/propylene glycol mixture without the need for heating, for example at a temperature between 15 and 35° C., advantageously at ambient temperature, in proportions which can range from 80/20 to 20/80 or even with glycerol in the same working conditions in proportions which can range from 80/20 to 20/80.

The insoluble material is removed by centrifugation and the aqueous-glycolic supernatant obtained is used preferably as such especially for preparing a cosmetic composition.

2.2) Determination of the Non-esterified Fatty Acids or NEFAs with the Commercial NEFA-C Determination Kit from Wako (from Oxoïd, 69571 Dardilly Cedex, France)

A study of the LPL inhibitory activity of a 2% St. John's wort extract was carried out at various concentrations fourfold. This 2% St John's wort extract was prepared by extracting 2 g of flower heads ground very finely in 98 g of an aqueous glycolic solvent mixture consisting of 40 weight percent of water/60 weight percent of butylene glycol, the insoluble material being removed by a centrifugation and the aqueous-glycolic supernatant obtained constituting the "2% St john's wort extract" used for the LPL inhibitory activity. The results obtained are listed in Table 7 below.

TABLE 7

| | Concentration of use 2% St. John's wort extract | | | | |
|---|---|---|---|---|---|
| | 5% | 3% | 2% | 1% | 0.5% |
| % inhibition with standard deviation in % | 96.5 ± 0.7 | 90.9 ± 0.8 | 76.9 ± 3.8 | 9.5 ± 1.7 | 5.7 ± 0.8 |

The percentages of inhibition obtained are listed in Table 7, which are measured by the determination of the NEFAs by the commercial NEFA-C determination kit from Wako as for the test of determination of *Uncaria tomentosa* mentioned above under b2) above.

The respective results of inhibition obtained with the extract of St. John's wort and the extract of *Uncaria tomentosa* are the subject of FIG. 3.

Figure 3:
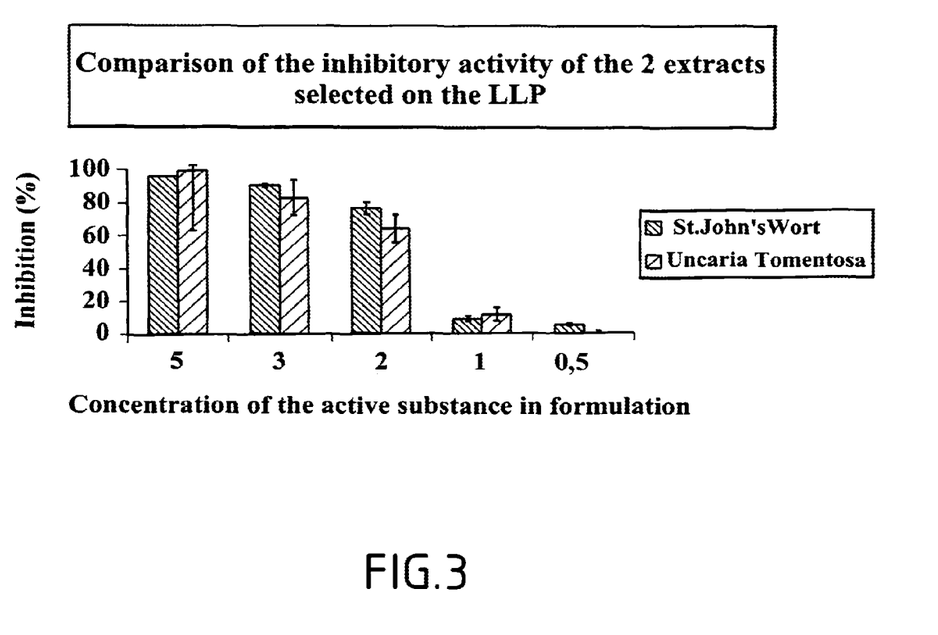

It can be noted from FIG. 3 that at the study concentrations, the results of the inhibition of LPL are roughly identical for the two extracts selected. Moreover, it can be added that the LPL-inhibiting activity of the extracts of liana and of St. John's wort is high and dose-dependent.

The screening of active products on the model of inhibition of the lipoprotein lipase developed by the inventors enables active products to be selected which inhibit this enzyme in a dose-dependent manner.

Amongst the active products which were selected, two extracts present spectacular effects: these are aqueous, glycolic or alcoholic extracts of two plants:

Peruvian liana called *Uncaria tomentosa*; and

St. John's wort.

Thus, the invention brings about particularly unexpected technical advantages which are not obvious to the person skilled in the art and which enable a novel method of tests to be provided which enable active products which are capable of being active upon lipoprotein lipase or LPL, to be selected.

The mention also covers the active products which are selected according to this method of testing, in particular extracts of liana and St. John's wort, for a cosmetic use in slimming, lipolytic, skin toning applications, etc.

The invention also covers cosmetic formulations which contain such active products, and their use as slimming creams.

The invention also covers the selection of pharmaceutically active products by the test method, which products can be the same active products or not as those which could have been selected within the context of a cosmetic activity, as well as the pharmaceutical formulations which contain such active products and their uses within the context of the treatment of a pathology in the field of lipolysis.

Examples of formulations of cosmetic compositions or pharmaceutical compositions are now described below.

EXAMPLES OF FORMULATION OF COSMETIC COMPOSITIONS OR PHARMACEUTICAL COMPOSITIONS

EXAMPLE 2

Use of the products of the invention in formulations of cosmetic or pharmaceutical compositions of the oil-in-water type.

Formulation 2a:

| | | |
|---|---|---|
| A | Water | qsp 100 |
| | Butylene Glycol | 2 |
| | Glycerine | 3 |
| | Sodium Dihydroxycetyl Phosphate, Isopropyl Hydroxycetyl Ether | 2 |
| B | Glycol Stearate SE | 14 |
| | Triisononanoine | 5 |
| | Octyl Cocoate | 6 |

-continued

| | | |
|---|---|---|
| C | Butylene Glycol, Methylparaben, Ethylparaben, Propylparaben, pH adjusted to 5.5 | 2 |
| D | Products of the invention | 0.01-30% |

Phases A and B are heated separately to 75° C., B is then added to A under vigorous stirring; C then D are then added, during the cooling of the cream thus formed.

Formulation 2b:

| | | |
|---|---|---|
| A | Water | qsp 100 |
| | Butylene Glycol | 2 |
| | Glycerine | 3 |
| | Polyacrylamide, Isoparaffin, Laureth-7 | 2.8 |
| B | Butylene Glycol, Methylparaben, Ethylparaben, Propylparaben; | 2 |
| | Phenoxyethanol, Methylparaben, Propylparaben, Butylparaben, Ethylparaben | 2 |
| | Butylene Glycol | 0.5 |
| C | Products of the invention | 0.01-30% |

Phase A is heated to 75° C.; B and then C are added to A with stirring, during the cooling of the formula thus prepared.

Formulation 2c:

| | | |
|---|---|---|
| A | Carbomer | 0.50 |
| | Propylene Glycol | 3 |
| | Glycerol | 5 |
| | Water | qsp 100 |
| B | Octyl Cocoate | 5 |
| | Bisabolol | 0.30 |
| | Dimethicone | 0.30 |
| C | Sodium Hydroxide | 1.60 |
| D | Phenoxyethanol, Methylparaben, Propylparaben, Butylparaben, Ethylparaben | 0.50 |
| E | Perfume | 0.30 |
| F | Products of the invention | 0.01-30% |

Phases A and B are heated separately to 75° C., and then B is added to A with vigorous stirring; C and then D then E then F are then added successively, during the cooling of the cream thus formed.

EXAMPLE 3 OF THE INVENTION

Use of the "lipolytic" products in a formulation of the water-in-oil type

| | | |
|---|---|---|
| A | PEG 30 - dipolyhydroxystearate | 3 |
| | Capric triglycerides | 3 |
| | Cetearyl Octanoate | 4 |
| | Dibutyl Adipate | 3 |
| | Grape seed oil | 1.5 |
| | Jojoba oil | 1.5 |
| | Phenoxyethanol, Methylparaben, Propylparaben, Butylparaben, ethylparaben | 0.5 |
| B | Glycerine | 3 |
| | Butylene Glycol | 3 |
| | Magnesium Sulphate | 0.5 |
| | EDTA | 0.05 |
| | Water | qsp 100 |
| C | Cyclomethicone | 1 |
| | Dimethicone | 1 |
| D | Perfume | 0.3 |
| E | Products of the invention | 0.01-30% |

Phases A and B are heated separately to 75° C., and then B is added to A with vigorous stirring; C and then D then E are then added, during the cooling of the cream thus formed.

EXAMPLE 4 OF THE INVENTION

Use of the "lipolytic" products in a formulation of the face cleanser type

| | | |
|---|---|---|
| A | Xanthane gum | 0.8 |
| | Water | qsp 100 |
| B | Butylene Glycol, Methylparaben, Ethylparaben, Propylparaben | 0.5 |
| | Phenoxyethanol, Methylparaben, Propylparaben, Butylparaben, ethylparaben | 0.5 |
| C | Citric acid | 0.8 |
| D | Sodium Laureth Sulphate | 40.0 |
| E | Product of the invention | 0.01-30% |

Phases A and B are prepared separately at ambient temperature, and then B is added to A with stirring; C and then D then E are then added, with moderate stirring.

EXAMPLE 5 OF THE INVENTION

Use of the products of the invention in a formulation of the anhydrous type

| | | |
|---|---|---|
| A | Mineral wax | 17.0 |
| | Isostearyl Isostearate | 31.5 |
| | Propylene Glycol Dipelargonate | 2.6 |
| | Propylene Glycol Isostearate | 1.7 |
| | Beeswax/PEG 8 | 3.0 |
| | Hydrogenated palm kernel oil | 3.4 |
| | Hydrogenated palm glycerides oil | |
| | Lanolin oil | 3.4 |
| | Sesame oil | 1.7 |
| | Cetyl Lactate | 1.7 |
| | Mineral oil, Lanoline alcohol | 3.0 |
| B | Castor oil | qsp 100 |
| | Products of the invention in dry form | 0.001-5% |

Phases A and B are heated separately to 80° C., and then B is added to A with stirring.

EXAMPLE 6 OF THE INVENTION

Use of the products of the invention in an aqueous gel formulation (face gels, body gels, etc.)

| | | |
|---|---|---|
| A | Water | qsp 100 |
| | Carboxyvinylic polymer (also called carbomer) | 0.5 |
| | Butylene Glycol | 15 |
| | Phenoxyethanol, Methylparaben, Propylparaben, Butylparaben, ethylparaben | 0.5 |
| B | Products of the invention | 0.01-30% |

Phase A is prepared by adding all the ingredients and by heating the whole to 80° C. up to the obtaining of a homogenous mixture. B is then added to A with vigorous stirring during the cooling of the gel thus formed.

EXAMPLE 7

Innocuousness Tests

Evaluation of the Cosmetic Acceptability of a Preparation Containing the Products of the Invention.

The toxicology tests were carried out on the two compounds retained, namely the extract of liana and the extract of St. John's wort, which are used pure, by an ocular evaluation in the rabbit, by a study of the absence of abnormal toxicity by a single oral administration in the rat, and by a study of the sensitizing power in the guinea pig.

1. Evaluation of the Primary Skin Irritation in the Rabbit:

The preparations described above are applied without dilution at the dose of 0.5 ml on the skin of 3 rabbits according to the method recommended by the OECD in relation to the « acute irritant/corrosive effect on the skin » study.

The products are classed according to the criteria defined by the Decision of the Jan. 2, 1982 published in the JORF (the « Journal Officiel de la République Française", the "Official Journal of the French Republic") of the Feb. 21, 1982.

The results of these tests have enabled concluding that the preparations retained were classed non-irritant for the skin.

2. Evaluation of the Ocular Irritation in the Rabbit:

The preparations described above were instilled pure and at once, at the rate of 0.1 ml, in the eye of 3 rabbits according to the method recommended by the Directive of the OECD No. 405 of the Feb. 24, 1987 in relation to the <<acute irritant/corrosive effect on the eye» study.

The results of this test have enabled concluding that the preparations can be considered as non-irritant for the eyes, in the sense of the Directive 91/326 EEC, used pure.

3. Test on the Absence of Abnormal Toxicity by Single Oral Administration in the Rat:

The preparations described were administered at once via the oral route at the dose of 5 g/Kg of body weight, to 5 male rats and 5 female rats according to a protocol inspired by the Directive of the OECD No. 401 of the 24 Feb. 1987 and adapted to the cosmetic products.

The LD0 and LD50 are found to be greater than 5,000 mg/Kg. The preparations tested are thus not classed amongst preparations which are dangerous by ingestion.

4. Evaluation of the Skin Sensitization Potential in the Guinea Pig:

The preparations described are subjected to the maximization test described by Magnusson and Kligmann, the protocol is in accordance with the Directive No. 406 of the OECD.

The preparations are classified as being non-sensitizing by contact with the skin.

The invention claimed is:

1. A method of skin care in a human in need of decreasing or slowing down fatty deposits in the skin of the human, in need of increasing blood microcirculation in the skin of the human, or in need of diminishing orange peel appearance in the skin of the human, comprising applying a composition of a hydro ethanolic bark extract of liana *Uncaria tomentosa* on the skin of the human in need thereof in an amount effective to decrease or slow down fatty deposits in the skin of the human in need thereof, to increase blood microcirculation in the skin of the human in need thereof, or to diminish orange peel appearance of the skin of the human in need thereof.

2. The method of claim 1, wherein the hydro ethanolic bark extract of liana *Uncaria tomentosa* inhibits lipoprotein lipase activity.

3. The method of claim 1, wherein the hydro ethanolic bark extract of liana *Uncaria tomentosa* is at a concentration between 0.01% and 70% by weight of the total composition.

4. The method of claim 1, wherein the hydro ethanolic bark extract of liana *Uncaria tomentosa* is at a concentration between 0.01% and 30% by weight of the total composition.

5. The method of claim 1, wherein the hydro ethanolic bark extract of liana *Uncaria tomentosa* is at a concentration between 0.5% and 20% by weight of the total composition.

6. The method of claim 1, wherein the composition is a cosmetic composition further comprising a cosmetically acceptable excipient.

7. The method of claim 1, wherein the composition is a pharmaceutical composition further comprising a pharmaceutically acceptable excipient.

8. The method of claim 1, wherein the composition is applied topically to a skin zone in need of decreasing or slowing down fatty deposits, in need of increasing blood microcirculation, or in need of diminishing orange peel appearance.

9. The method of claim 8, wherein said skin zone is a skin zone of the body.

* * * * *